United States Patent [19]
Maeda et al.

[11] Patent Number: 5,501,860
[45] Date of Patent: Mar. 26, 1996

[54] HEMICELLULOSE BINDER AND PRODUCT USING THE SAME

[75] Inventors: Hirokazu Maeda; Hitoshi Furuta; Taro Takahashi, all of Ibaraki; Hiroshi Shimizu, Suita, all of Japan

[73] Assignee: Fuji Oil Co., Ltd., Osaka, Japan

[21] Appl. No.: 211,510

[22] PCT Filed: Aug. 6, 1993

[86] PCT No.: PCT/JP93/01112

§ 371 Date: Mar. 31, 1994

§ 102(e) Date: Mar. 31, 1994

[87] PCT Pub. No.: WO94/03071

PCT Pub. Date: Feb. 17, 1994

[30] Foreign Application Priority Data

| Aug. 7, 1992 | [JP] | Japan | 4-232996 |
| Jan. 29, 1993 | [JP] | Japan | 5-012996 |
| May 17, 1993 | [JP] | Japan | 5-114310 |

[51] Int. Cl.$^6$ .............................. A61K 9/16; A61K 9/20
[52] U.S. Cl. .................. 424/464; 424/465; 424/489
[58] Field of Search ........................ 424/464, 465, 424/470, 474, 479, 480, 489, 493, 494

[56] References Cited

U.S. PATENT DOCUMENTS

| 4,927,649 | 5/1990 | Antenucci ........................ 426/273 |
| 5,151,273 | 9/1992 | Korsatko-Wabnegg et al. ....... 424/465 |

FOREIGN PATENT DOCUMENTS

| 0128666 | 12/1984 | European Pat. Off. . |
| 0272119 | 6/1988 | European Pat. Off. . |
| 0301440 | 2/1989 | European Pat. Off. . |
| 57-036947 | 2/1982 | Japan . |
| 59-011153 | 1/1984 | Japan . |
| 61-231950 | 10/1986 | Japan . |
| 4-197138 | 7/1992 | Japan . |
| 4-185681 | 7/1992 | Japan . |
| 04197138 | 7/1992 | Japan . |
| 4-325058 | 11/1992 | Japan . |
| 5007449 | 1/1993 | Japan . |
| WO90/05460 | 5/1990 | WIPO . |

*Primary Examiner*—Thurman K. Page
*Assistant Examiner*—James M. Spear
*Attorney, Agent, or Firm*—Wallenstein & Wagner, Ltd.

[57] ABSTRACT

A binder comprising as an active ingredient a water-soluble hemicellulose derived from beans, a sugar coating composition comprising the binder, a sugar coated composition coated with the sugar coating composition and a granulated product and a tableted product each containing the binder.

8 Claims, No Drawings

HEMICELLULOSE BINDER AND PRODUCT USING THE SAME

TECHNICAL FIELD

The present invention relates to a binder and a product using the same. More particularly, it is concerned with a binder comprising as an active ingredient a water-soluble hemicellulose derived from beans, a sugar coating composition comprising said binder, a sugar coated composition comprising a composition coated with said sugar coating composition, granules of powder prepared in the production of lemonade-flavored confectionery and tablets containing said binder and tableted products provided by tableting the granules.

In the present invention, the term "sugar coat" is intended to mean a sweet coating containing sugar, which coating is applied to confectionery and tablets. The term "sugar coating composition" is intended to mean a composition for the production of the sugar coating. The term "sugar coated composition" is intended to mean a composition having a sugar coating such as sugar coated confectionery or tablets.

BACKGROUND ART

In sugar coated confectionery, such as marble chocolates, and sugar coated tablets, such as pharmaceuticals, a coating of a saccharide, such as sugar, is formed on the surface of a material to protect the material or render the material easy to eat or swallow. The sugar coating is usually effected as follows. An aqueous sugar solution is mixed with an assistant comprising a polysaccharide, such as gum arabic, chemically modified starch or dextrin, or a protein, such as gelatin, to prepare a sugar solution having high viscosity and concentration. This sugar solution is put on a material to be coated in a rotary kiln and subjected to forced draft drying. This procedure is repeated several times to form a coating.

On the other hand, tableted confectionery, such as lemonade-flavored confectionery, and tablets, such as pharmaceuticals, are produced by kneading various powdery raw materials as main ingredients with a solution of a binder, such as gum arabic, or granulating the main ingredients, effecting compression molding, such as tableting, and optionally drying the tablets. In the tableted confectionery and tablets prepared without use of any binder, partial breaking or cracking occurs due to physical force applied internally or externally during production or storage after the production. On the other hand, when a binder is used and granules of powder are prepared prior to tableting, use of the binder is indispensable because if good granules having a homogeneous size cannot be prepared, the subsequent workability would become poor. The gum arabic used as the binder is obtained by refining exudates of trees belonging to the genus Acacia.

In recent years, however, the production of the gum arabic has been sharply decreased due to abnormal weather and a change of government in the Sudan, a main gum arabic producing country. This has resulted in an increase in price of the gum arabic and produced sharp fluctuations in the production and price of the gum arabic. Binders, which are stable in price, include gelatin and dextrin. However, the binding force thereof is so low that, during the sugar coating operation, cracking occurs on the surface of the sugar coating or sugar coating comes off. Further, good granules as described above cannot be prepared using gum arabic and polysaccharides such as dextrin. For this reason, sugar coating compositions, which can provide a high coating strength, can be stably supplied and are inexpensive, and binders for granules and tableted products, which have a high binding force, enable good granules to be prepared before tableting, are naturally occurring, have a low price and can be produced stably, have been desired in the art.

DISCLOSURE OF THE INVENTION

An object of the present invention is to provide a binder which, in coating of sugar on confectionery or tablets, exhibits a workability, a coat forming property and a sugar coating strength equivalent or superior to assistants such as gum arabic, which can be stably supplied and is inexpensive, and a sugar coating composition, a granulated product and a tableted product using the same.

In view of the above, the present inventors have made extensive and intensive studies and, as a result, have found that when a water-soluble hemicellulose derived from beans is used as a binder, a sugar coating composition having good workability and excellent coat formability and sugar coating strength can be provided, granulation of powder necessary for the production of tableted confectionery and tablets can be successfully effected, breaking or cracking after tableting is less likely to occur and, at the same time, when the product is eaten or administered, the feeling of eating and disintegration can compare favorably with that obtained when use is made of other binders. The present invention has been made based on such findings.

Accordingly, the present invention relates to a binder composed mainly of a water-soluble hemicellulose derived from beans, a sugar coating composition using the binder, a sugar coated composition comprising a composition coated with the sugar coating composition and a granulated product and a tableted product using the binder.

BEST MODE FOR CARRYING OUT THE INVENTION

In the present invention, the water-soluble hemicellulose is preferably derived from beans, particularly soybeans, especially the cotyledons thereof.

Although the water-soluble hemicellulose derived from beans may have any molecular weight, the average molecular weight is preferably in the range of from several tens of thousands to several millions, specifically in the range of from 50,000 to one million. When the average molecular weight is less than 50,000, the binding property is poor. On the other hand, when the average molecular weight exceeds one million, the workability in the production of the tableted confectionery and tablets becomes poor and there is a tendency that when the product is eaten or administered, the degradation of the product is locally so poor that the feeling of eating is spoiled or the efficacy is lowered. The average molecular weight of the water-soluble hemicellulose is a value determined by the limiting viscosity method wherein the viscosity is measured in a 0.1M $NANO_3$ solution using a standard pullulan (manufactured by Showa Denko K.K.).

The water-soluble hemicellulose derived from beans according to the present invention can be produced by extracting the water-soluble hemicellulose from a raw material containing hemicelluloses with water or in some cases, by heat-eluting the hemicellulose therefrom under acidic or alkaline conditions or decomposition-eluting the hemicellulose therefrom with an enzyme. An embodiment of the above-described process for producing the water-soluble hemicellulose will now be described.

A polysaccharide residue obtained usually by removing fats and oils, proteins and starch from beans, for example, soybeans and peas, can be used as the raw material. When soybeans are used as the raw material, "okara" (bean-curd refuse) produced as a by-product in the production of bean curd, soybean milk or separated soybean protein may be utilized as the raw material.

The above-described raw material is heat-decomposed under acidic or alkaline conditions, preferably in a pH region around the isoelectric point of each protein, preferably at 80° to 130° C., still preferably 100° to 130° C., to fractionate a water-soluble fraction which is then dried as it is or alternatively subjected to, for example, an activated carbon treatment, a resin adsorption treatment or an ethanol precipitation treatment to remove hydrophobic substances or low-molecular weight substances and dried to provide a water-soluble hemicellulose.

When the bean-derived water-soluble hemicellulose thus produced is added to a sugar coating composition before use, the amount of the water-soluble hemicellulose added is preferably in the range of from 1 to 30% by weight, still preferably in the range of from 2 to 20% by weight, based on the whole sugar composition. Even though the amount of the water-soluble hemicellulose added is outside the above range, it is possible to effect sugar coating. However, when the amount of the water-soluble hemicellulose added is small depending upon the amount of sugar, the strength of the coating is so low that the sugar coating is likely to crack or comes off. On the other hand, when the amount of the water-soluble hemicellulose is excessively large, there is a tendency that the necessary drying time becomes longer.

Granules or tableted products may be produced according to the conventional process for producing granule products, tableted confectionery or tablets. In this case, the bean-derived hemicellulose according to the present invention may be used instead of polysaccharides, such as gum arabic, and gelatin which are usually used as binders for granules or tableted products. That is, a binder solution is previously prepared using the hemicellulose. The concentration of the binder solution is generally in the range of from 5 to 30%, preferably in the range of from 5 to 20%. When it is excessively high, the workability become poor because the viscosity becomes high. On the other hand, when the concentration is excessively low, the binding force is so low that it becomes difficult to provide good granules or tableted products.

The binder solution is sprayed on a powdery raw material mixture while drying or alternatively added to and well kneaded with a powdered raw material mixture. The amount of the binder solution used is not particularly limited. It, however, is preferably in the range of from 0.5 to 10% by weight on a dry basis based on the whole mixture. When the amount is less than 0.5% by weight, the binding property of the binder is unsatisfactory. On the other hand, when it exceeds 10% by weight, good granules cannot be prepared or there is a tendency that feeling of eating or degradation of the tableted confectionery and tablets is deteriorated. Thereafter, the treated product is applied to a tablet machine and subjected to tableting. After tableting, the resultant tablets are dried according to need.

In the present invention, the water-soluble hemicellulose derived from beans, as such, can be used usefully as an assistant for a sugar coating composition. However, no problem arises when it is used in combination with other materials, i.e., gum arabic, polysaccharides, such as chemically modified starch, sodium alginate, pullulan and polyvinylpyrrolidone, and proteins, such as gelatin.

In the present invention, if necessary, the hemicellulose derived from beans may be used in combination with other binders. Examples of the other binders include general gums represented by gum arabic, starch and chemically modified starch and proteinaceous materials represented by gelatin.

The present inventors think that the effect of the present invention is based on such a phenomenon that the coat formability after drying is excellent by virtue of the molecular weight or structure of the water-soluble hemicellulose derived from beans and, further, since the formed coat has moisture retention to some extent, the product becomes flexible.

As disclosed in Japanese Unexamined Patent Publication (Kokai) No. 62-32844, in the production of tableted confectionery, when an emulsion comprising a water-soluble organic polymer compound as a binder, an emulsifier and fat and oil is used to provide tableted confectionery which is soft and pleasant to the tongue, since the hemicellulose derived from beans according to the present invention, as such, has a emulsifying property, the desired effect can be attained without use of any emulsifier.

As described above, the sugar coating composition produced using as a binder the hemicellulose derived from beans has excellent workability, coat formability and adhesion, and granulated products and tableted products using the binder have an excellent binding capacity and are less liable to cause breaking or cracking during the production or storage.

The present invention will now be described in more detail with reference to the following examples which are presented for illustrative purposes only and are not intended to limit the spirit and scope of the invention. In the following examples, all "parts" and "%" are by weight.

Preparation Water-Soluble Soybean Hemicullulose (SSHC)

To raw okara provided by an isolated soybean protein production process was added water in an amount of twice the amount of the raw okara. The mixture was adjusted to pH 4.5 with hydrochloric acid and hydrolyzed at 120° C. for 1.5 hr. The reaction mixture was cooled and centrifuged (10000 G×30 min) to separate it into a supernatant and a precipitate. The separated precipitate was further washed with an equal weight of water and centrifuged, and the resultant supernatant was combined with the above supernatant, applied to an activated carbon column and dried to provide SSHC (i). Separately, SSHC (ii) was provided in the same manner as that described above, except that the treatment using an activated carbon column was not effected.

Further, SSHC (i) was dissolved in 0.5% saline, and reprecipitation was repeated three times in such a manner that the ethanol concentration became 50%, followed by desalting with an ion-exchange resin ("Amberlite IR-120 B" manufactured by Organo Corp.) to provide SSHC (iii).

The percentage composition of the resultant SSHC's was as follows.

| Components | Composition (%) | | |
| --- | --- | --- | --- |
| | (i) | (ii) | (iii) |
| Water | 5.71 | 5.10 | 7.75 |
| Crude protein | 5.93 | 5.43 | 1.03 |
| Crude ash | 5.29 | 5.30 | 0.22 |
| Polysaccharides | 87.07 | 84.17 | 91.00 |

-continued

| Components | Composition (%) | | |
|---|---|---|---|
| | (i) | (ii) | (iii) |
| Average molecular weight | 178,000 | 114,000 | 207,000 |

Then, the saccharide composition of the SSHC's (i), (ii) and (iii) was analyzed. In the analysis, uronic acid was measured by the Blumenkrantz method, and neutral saccharides were measured by the alditol acetate method.

The results were as follows.

| Kind of saccharides | Composition of Saccharides (%) | | |
|---|---|---|---|
| | (i) | (ii) | (iii) |
| Uronic acid | 20.4 | 19.4 | 16.9 |
| Rhamnose | 1.6 | 2.1 | 2.7 |
| Fucose | 2.7 | 3.9 | 5.2 |
| Arabinose | 19.9 | 23.1 | 19.2 |
| Xylose | 6.4 | 5.8 | 8.4 |
| Galactose | 47.3 | 43.4 | 46.8 |
| Glucose | 1.8 | 2.3 | 0.9 |

EXAMPLE 1

A chocolate was subjected to sugar coating with a sugar coating compositions of a formulation using SSHC (i) specified in the following table. For comparison, sugar coating was effected in the same manner as that described above, except that use was made of gum arabic (manufactured by Kishida Reagents Chemical Co., Ltd.), chemically modified starch (Foodrex manufactured by Matsutani Kagaku Kogyo Co., Ltd.) which were commonly used in the art.

The sugar coating composition was dusted onto a spherical chocolate, which had been charged in a rotary kiln, according to the conventional method. Powdered sugar was dusted and adhered onto the surface of the sugar coating composition, and forced draft drying was effected. Thereafter, a series of steps, i.e., the step of dusting the sugar coating composition, the step of dusting and adhering powdered sugar and the step of effecting forced draft drying, were repeated four times. The product was finally subjected to shellac coating to provide sugar coated chocolate confectionery.

| Formulation | Formulation of Sugar Coating Solution (Parts.) | | |
|---|---|---|---|
| | Ex. 1 | Comp. Ex. 1 | Comp. Ex. 2 |
| SSHC | 10 | — | — |
| Gum arabic | — | 15 | — |
| Foodtex | — | — | 15 |
| Sugar | 60 | 60 | 60 |
| Water | 25 | 25 | 25 |

The sugar coated chocolate confectionery was evaluated. The results were as follows.

| Evaluation | Results of Evaluation | | |
|---|---|---|---|
| | Ex. 1 | Comp. Ex. 1 | Comp. Ex. 2 |
| Coat forming property | Good | Good | Somewhat good |
| Falling | None | None | None |
| Cracking | None | None | Somewhat cracked |
| Drying | Easy | Easy | Easy |

From the above results, it is apparent that the sugar coating composition using SSHC exhibits good results despite the fact that the amount of SSHC used is smaller than the amount of the commercially available gum arabic.

EXAMPLE 2

A sugar coating test was carried out in a rotary kiln for sugar coating, using 20000 dummy bare tablets each comprising lactose and starch and having a diameter of 7 mm and a weight of 120 mg and sugar coating composition solutions prepared according to the following formulations. In this case, in the comparative examples, pullulan, gum arabic or gelatin was used instead of SSHC. The sugar coating strength of the sugar coated tablets was evaluated by a drop test.

| Formulation | Formulation of Sugar Coating Solution (Parts.) | | | | |
|---|---|---|---|---|---|
| | Ex. 2 | Comp. Ex. 3 | Comp. Ex. 4 | Comp. Ex. 5 | Comp. Ex. 6 |
| (Solution for undercoat) | | | | | |
| SSHC | 1 | — | — | — | — |
| Pullulan | — | 1 | — | — | — |
| Gelatin | — | — | 1 | — | — |
| Gum arabic | — | — | — | 1 | 3 |
| Sugar | 79 | 79 | 79 | 79 | 77 |
| Water | 20 | 20 | 20 | 20 | 20 |
| (Solution for smoothing layer) | | | | | |
| Undercoat described above | 100 | 100 | 100 | 100 | 100 |
| Precipitated calcium carbonate | 50 | 50 | 50 | 50 | 50 |
| Powdered sugar | 10 | 10 | 10 | 10 | 10 |
| Talc | 10 | 10 | 10 | 10 | 10 |
| (Solution for overcoat) | | | | | |
| Sugar | 65 | 65 | 65 | 65 | 65 |
| Gelatin | 1 | 1 | 1 | 1 | 1 |
| Water | 34 | 34 | 34 | 34 | 34 |

Sugar coating was carried out as follows.

At the outset, with respect to the undercoat, a series of steps, that is, the step of applying the solution for an undercoat onto the tablets in the number of times and the solution amount specified in the following table, the step of spreading talc over the coated tablets and the step of drying the tablets were repeated 13 times.

| Undercoat Treatment | | |
| --- | --- | --- |
| Number of times of spreading | Amount of solution for undercoat (g) | Talc (g) |
| 1 | 300 | 150 |
| 1 | 400 | 60 |
| 3 | 650 | 80 |
| 8 | 750 | 90 |

Then, with respect to the smoothing layer, a series of steps, that is, the step of applying the solution for a smoothing layer onto the undercoat of the tablets in the number of times and the solution amount specified in the following table and the step of drying the coated tablets were repeated 20 times.

| Smoothing Layer Treatment | |
| --- | --- |
| Number of times of spreading | Amount of solution for smoothing layer (g) |
| 1 | 100 |
| 1 | 90 |
| 13 | 80 |
| 5 | 60 |

Thereafter, with respect to the overcoat, a series of steps, that is, the step of applying the solution for an overcoat onto the smoothing layer of the tablets in the number of times and the solution amount specified in the following table and the step of drying the coated tablets were repeated 15 times.

| Overcoat Treatment | |
| --- | --- |
| Number of times of spreading | Amount of solution for overcoat (g) |
| 1 | 250 |
| 14 | 200 |

Drop Test 500 sugar coated tablets as prepared above were placed in a plastic container and dropped on concrete from a height of 1 m to determine the number of broken tablets.

| Results of Drop Test | |
| --- | --- |
| Sugar coated tablet | Number of broken tablets |
| Ex. 2 | 11 |
| Comp. Ex. 3 | 35 |
| Comp. Ex. 4 | 52 |
| Ccmp. Ex. 5 | 55 |
| Comp. Ex. 6 | 42 |

From the above results, it is apparent that sugar coated tablets subjected to sugar coating with the sugar coating composition according to the present invention has an excellent sugar coating strength and a good sugar coating surface luster. In addition, they had no problem also in the breaking rate.

The above procedure of the Example was repeated, except that SSHC (ii) and SSHC (iii) were used instead of SSHC (i).

The results were substantially equivalent to those obtained for SSHC (i).

EXAMPLE 3 AND COMPARATIVE EXAMPLE 7

Lemonade-flavored confectionery was prepared according to the following formulations using SSHC (i) or gum arabic (Control) instead of SSHC (i) or neither SSHC (i) nor gum arabic for comparative purposes (Comparative Example 7) to observe the state in the tableting, state in the drop test and degradation of the tablets. Tableting of the lemonade-flavored confectionery was carried out by molding the composition using a lemonade-flavored molding machine at 23 kg/cm$^2$ into a single cylinder form having a diameter of 8 mm and a thickness of 6 mm and drying the molding at 80° C. for 60 min. In the drop test, 100 granules were packed into a polyethylene bottle and subjected to gravity dropping from a height of 100 cm to observe the state of cracking. The degradation was determined by measuring the rate of degradation in warm water at 37° C. using a degradation tester (average of 10 data).

| Formulation of Lemonade-flavored Confectionery (Parts.) | | | |
| --- | --- | --- | --- |
| Ingredients | Ex. 3 | Control | Comp. Ex. 7 |
| Powdered sugar | 80 | 80 | 80 |
| Corn starch | 20 | 20 | 20 |
| Sodium bicarbonate | 0.6 | 0.6 | 0.6 |
| 20% aqueous solution of SSHC | 5 | — | — |
| 20% aqueous solution of gum arabic | — | 5 | — |
| Water | — | — | 4 |
| Acidulant | 0.4 | 0.4 | 0.4 |

The results of evaluation were as follows.

| Results of Evaluation | | | |
| --- | --- | --- | --- |
| Evaluation | Ex. 3 | Control | Comp. Ex. 7 |
| (During tableting) | | | |
| Adhesion to pestle and mortar | None | None | None |
| Cracking (Drop test (per 100 tablets)) | None | None | Cracked |
| Somewhat broken | 11 | 14 | 34 |
| Significantly broken | 5 | 12 | 15 |
| Cracking | 1 | 5 | 13 |
| Degradation (sec) | 52 | 54 | 43 |

As is apparent from the evaluation results, when SSHC (i) was used as the binder, the state in tableting and degradation could compare favorably with those obtained when the gum arabic was used as the binder. Further, the results of the drop test were superior to those obtained when the gum arabic was used as the binder. Further, all the results of the state in tableting, drop test and degradation were superior to those of Comparative Example 1 wherein no binder was used.

EXAMPLE 4

A 10 wt. % aqueous solution of SSHC (i) was prepared and sprayed on powdered sugar to prepare powdered sugar granules. A powdered perfume was added to the granules, and the mixture was subjected to tableting at 200 kg/cm² to provide tablets having a diameter of 16 mm which were then dried to provide tableted confectionery. For comparison, the above procedure was repeated, except that a 10 wt. % aqueous solution of gum arabic (control) or water alone (Comparative Example 8) was used instead of the 10 wt. % aqueous solution of SSHC (i).

The state of the granules, state in the tableting, state in the drop test and degradation were observed in the same manner as that described above.

Formulations and evaluation results are given in the following tables.

Formulation of Tableted Confectionery (Parts.)

| Ingredients | Ex. 4 | Control | Comp. Ex. 8 |
|---|---|---|---|
| Powdered sugar | 100 | 100 | 100 |
| 10% aqueous solution of SSHC | 10 | — | — |
| 10% aqueous solution of gum arabic | — | 10 | — |
| Water | — | — | 10 |
| Powdered perfume | 1 | 1 | 1 |

Results of Evaluation

| Evaluation | Ex. 4 | Control | Comp. Ex. 8 |
|---|---|---|---|
| (State of granules) | | | |
| Homogeneity of size | Homogeneous | Somewhat homogeneous | Heterogeneous |
| Fluidity | Good | Somewhat good | Poor |
| (During tableting) | | | |
| Adhesion to pestle and mortar | None | None | None |
| Cracking (Drop test (per 100 tablets)) | None | None | Cracked |
| Somewhat broken | 1 | 1 | 10 |
| Significantly broken | 0 | 0 | 3 |
| Cracking | 0 | 0 | 3 |
| Degradation (sec) | 85 | 88 | 75 |

As is apparent from the above results, as with Example 3, the tableted confectionery produced by the above method has no problem of workability, such as cracking during tableting. Further, the tableted confectionery had a strength equal to that using gum arabic. From the above results, it is estimated that even when SSHC (i) is used in tablets or the like obtained by tableting using formulations similar to that used in Example 4, the results would be equivalent to those obtained in Example 4. In particular, the granules of powder prepared prior to tableting were superior to those prepared using gum arabic in homogeneity of the size and fluidity. For this reason, it is considered that granulation using SSHC (i) could be applied widely to granulation of powder.

EXAMPLE 5

A 10 wt. % aqueous SSHC (i) solution was prepared. Further, for comparison, an aqueous gum arabic solution was prepared as a control. 95 parts of each of the aqueous solution was heated, and 5 parts of a vegetable fat and oil having a melting point of 38° C. was added thereto for emulsification. The emulsified solutions were sprayed on powdered sugar to prepare powered sugar granules. A powdered perfume was added to the granules, and the mixture was subjected to tableting at 200 kg/cm² to provide tablets each having a diameter of 16 mm, thereby producing tableted confectionery.

Formulations and evaluation results were as follows.

Formulation of Tableted Confectionery

| Ingredients | Ex. 5 | Control |
|---|---|---|
| Powdered sugar | 100 | 100 |
| Emulsifying solution of SSHC | 10 | — |
| Emulsifying solution of gum arabic | — | 10 |
| Powdered perfume | 1 | 1 |

Results of Evaluation

| Evaluation | Ex. 5 | Control |
|---|---|---|
| (State of granules) | | |
| Homogeneity of size | Homogeneous | Homogeneous |
| Fluidity | Good | Somewhat good |
| (During tableting) | | |
| Adhesion to pestle and mortar | None | None |
| Cracking (Drop test (per 100 tablets)) | None | None |
| Somewhat broken | 2 | 2 |
| Significantly broken | 0 | 0 |
| Cracking | 0 | 0 |
| Degradation (sec) | 78 | 75 |

As is apparent from the above results, as with Example 3, the tableted confectionery produced by the above method has no problem of workability, such as cracking during tableting. Further, the tableted confectionery had a strength equal to that using gum arabic. Further, as a result of a sensory test, it was found that also when SSHC (i) was used, the resultant tableted confectionery was soft and pleasant to the tongue and smooth as with that obtained using gum arabic. From this fact, it was confirmed that when an emulsion prepared using SSHC (i) was used, the effect attained was equivalent to that of the control using gum arabic.

The procedure of each Example was repeated, except that SSHC (ii) and SSHC (iii) were used instead of SSHC (i). The results were substantially the same as those obtained when SSHC (i) was used.

INDUSTRIAL APPLICABILITY

The water-soluble hemicellulose derived from beans according to the present invention can be produced relatively simply and economically. Further, since beans are agricultural products of which the production in the world is high, they can be stably supplied. Further, when the water-soluble hemicellulose derived from the beans are used in the sugar coating composition, products having excellent adhesion and film formability can be provided. This effect can compare favorably with gum arabic which exhibits the best effect as the sugar coating composition. Further, when the above water-soluble hemicellulose is used as the binder for granulated products and tableted products, it becomes possible to produce granulated products having excellent homogeneity in size or shape and fluidity and tableted products having excellent qualities in respect of binding property and the like.

We claim:

1. A sugar coating composition consisting of an aqueous solution of sugar and a binder as an active ingredient, the binder comprising water-soluble hemicellulose derived from soybeans, the water-soluble hemicellulose having an average molecular weight in the range of 50,000 to one million and being added to the sugar coating composition in the range of 1 to 30% by weight.

2. A sugar coating composition consisting of an aqueous solution of sugar and a binder according to claim 1, wherein said water-soluble hemicellulose is derived from soybean cotyledon.

3. A sugar coated composition comprising a composition coated with a sugar coating composition according to claim 1.

4. A sugar coated composition comprising a composition coated with a sugar coating composition according to claim 2.

5. A granulated product comprising a binder according to claim 1.

6. A granulated product comprising a binder according to claim 2.

7. A tableted product comprising a binder according to claim 1.

8. A tableted product comprising a binder according to claim 2.

* * * * *